(12) United States Patent
Greenberg

(10) Patent No.: US 8,002,816 B2
(45) Date of Patent: Aug. 23, 2011

(54) PROSTHESIS FOR IMPLANTATION IN AORTA AND METHOD OF USING SAME

(75) Inventor: Roy K. Greenberg, Bratenahl, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 12/336,732

(22) Filed: Dec. 17, 2008

(65) Prior Publication Data

US 2009/0222078 A1    Sep. 3, 2009

Related U.S. Application Data

(60) Provisional application No. 61/008,949, filed on Dec. 21, 2007.

(51) Int. Cl.
*A61F 2/06* (2006.01)
(52) U.S. Cl. ...................................... 623/1.13
(58) Field of Classification Search ......... 623/1.11–1.48
See application file for complete search history.

(56) References Cited

U.S. PATENT DOCUMENTS

| | | |
|---|---|---|
| 5,104,404 A | 4/1992 | Wolff |
| 5,123,917 A | 6/1992 | Lee |
| 5,387,235 A | 2/1995 | Chuter |
| 5,522,880 A | 6/1996 | Barone et al. |
| 5,571,173 A | 11/1996 | Parodi |
| 5,578,071 A | 11/1996 | Parodi |
| 5,591,229 A | 1/1997 | Parodi |
| 5,607,444 A | 3/1997 | Lam |
| 5,617,878 A | 4/1997 | Taheri |
| 5,693,087 A | 12/1997 | Parodi |
| 5,720,776 A | 2/1998 | Chuter et al. |
| 5,921,995 A | 7/1999 | Kleshinski |
| 5,961,548 A | 10/1999 | Shmulewitz |
| 5,984,955 A | 11/1999 | Wisselink |
| 6,010,530 A | 1/2000 | Golcoechea |
| 6,030,414 A | 2/2000 | Taheri |
| 6,053,941 A | 4/2000 | Lindenberg et al. |
| 6,056,700 A | 5/2000 | Burney et al. |
| 6,059,824 A | 5/2000 | Taheri |
| 6,074,416 A | 6/2000 | Berg et al. |
| 6,077,296 A | 6/2000 | Shokoohi et al. |
| 6,102,940 A | 8/2000 | Robichon et al. |

(Continued)

FOREIGN PATENT DOCUMENTS

EP     0 461 791 B1    1/1997

(Continued)

OTHER PUBLICATIONS

International Search Report for International Application No. PCT/US2008/087145, dated Mar. 4, 2009, 5 pages.

*Primary Examiner* — Suzette J Gherbi
(74) *Attorney, Agent, or Firm* — Brinks Hofer Gilson & Lione

(57) ABSTRACT

Prosthesis for implantation in the ascending aorta comprising a tubular body made of biocompatible graft material, a cuff at the proximal portion of the tubular body for biasing pressure onto a sino-tubular junction and that is configured to conform to the junction. A stent assembly can also be used to the prosthesis to bias pressure on the wall of a dissection to substantially deflate a false lumen.

3 Claims, 10 Drawing Sheets

U.S. PATENT DOCUMENTS

| | | | |
|---|---|---|---|
| 6,152,944 | A | 11/2000 | Holman et al. |
| 6,152,956 | A | 11/2000 | Pierce |
| 6,168,621 | B1 | 1/2001 | Vrba |
| 6,171,329 | B1 | 1/2001 | Shaw et al. |
| 6,176,875 | B1 | 1/2001 | Lenker et al. |
| 6,187,033 | B1 | 2/2001 | Schmitt et al. |
| 6,210,429 | B1 | 4/2001 | Vardi et al. |
| 6,217,609 | B1 | 4/2001 | Haverkost |
| 6,221,090 | B1 | 4/2001 | Wilson |
| 6,238,430 | B1 | 5/2001 | Klumb et al. |
| 6,290,731 | B1 | 9/2001 | Solovay et al. |
| 6,325,819 | B1 | 12/2001 | Pavcnik et al. |
| 6,325,826 | B1 | 12/2001 | Vardi et al. |
| 6,334,869 | B1 | 1/2002 | Leonhardt et al. |
| 6,344,056 | B1 | 2/2002 | Dehdashtian |
| 6,409,756 | B1 | 6/2002 | Murphy |
| 6,409,757 | B1 | 6/2002 | Trout, III et al. |
| 6,428,565 | B1 | 8/2002 | Wisselink |
| 6,471,672 | B1 | 10/2002 | Brown et al. |
| 6,482,227 | B1 | 11/2002 | Solovay |
| 6,517,574 | B1 | 2/2003 | Chuter |
| 6,524,335 | B1 | 2/2003 | Hartley et al. |
| 6,541,050 | B1 | 4/2003 | Bonorden et al. |
| 6,572,648 | B1 | 6/2003 | Klumb et al. |
| 6,582,394 | B1 | 6/2003 | Reiss et al. |
| 6,585,758 | B1 | 7/2003 | Chouinard et al. |
| 6,585,762 | B1 * | 7/2003 | Stanish ............ 623/1.3 |
| 6,645,242 | B1 | 11/2003 | Quinn |
| 6,652,567 | B1 | 11/2003 | Deaton |
| 6,663,667 | B2 | 12/2003 | Dehdashtian et al. |
| 6,669,720 | B1 | 12/2003 | Pierce |
| 6,695,877 | B2 | 2/2004 | Brucker et al. |
| 6,706,062 | B2 | 3/2004 | Vardi et al. |
| 6,723,116 | B2 | 4/2004 | Taheri |
| 6,733,522 | B2 | 5/2004 | Schmitt et al. |
| 6,733,523 | B2 | 5/2004 | Shaolian et al. |
| 6,767,358 | B2 | 7/2004 | Leonhardt et al. |
| 6,773,457 | B2 | 8/2004 | Ivancev et al. |
| 6,814,752 | B1 * | 11/2004 | Chuter ............ 623/1.35 |
| 7,041,127 | B2 * | 5/2006 | Ledergerber ............ 623/1.31 |
| 2001/0027338 | A1 | 10/2001 | Greenberg |
| 2002/0052648 | A1 | 5/2002 | McGuckin, Jr. et al. |
| 2002/0072790 | A1 | 6/2002 | McGuckin et al. |
| 2002/0082684 | A1 | 6/2002 | Mishaly |
| 2002/0099441 | A1 | 7/2002 | Dehdashtian |
| 2002/0144696 | A1 | 10/2002 | Sharawy et al. |
| 2002/0156517 | A1 | 10/2002 | Perouse |
| 2002/0156522 | A1 | 10/2002 | Ivancev et al. |
| 2002/0193872 | A1 | 12/2002 | Trout, III et al. |
| 2002/0198585 | A1 * | 12/2002 | Wisselink ............ 623/1.11 |
| 2003/0033005 | A1 | 2/2003 | Houser et al. |
| 2003/0074050 | A1 | 4/2003 | Kerr |
| 2003/0093145 | A1 | 5/2003 | Lawrence-Brown et al. |
| 2003/0120333 | A1 | 6/2003 | Ouriel et al. |
| 2003/0130720 | A1 | 7/2003 | De Palma et al. |
| 2003/0130724 | A1 | 7/2003 | De Palma et al. |
| 2003/0135257 | A1 | 7/2003 | Taheri ............ 623/1.11 |
| 2003/0199967 | A1 | 10/2003 | Hartley et al. |
| 2003/0199973 | A1 | 10/2003 | Chuter et al. |
| 2003/0220682 | A1 | 11/2003 | Kujawski |
| 2003/0225453 | A1 | 12/2003 | Murch |
| 2004/0024446 | A1 | 2/2004 | Smith |
| 2004/0034406 | A1 | 2/2004 | Thramann |
| 2004/0044396 | A1 | 3/2004 | Clerc et al. |
| 2004/0059406 | A1 | 3/2004 | Cully et al. |
| 2004/0064081 | A1 * | 4/2004 | Stanish ............ 604/8 |
| 2004/0073288 | A1 | 4/2004 | Kerr |
| 2004/0093078 | A1 | 5/2004 | Moll et al. |
| 2004/0106972 | A1 | 6/2004 | Deaton |
| 2004/0117003 | A1 * | 6/2004 | Ouriel et al. ............ 623/1.35 |
| 2004/0117004 | A1 | 6/2004 | Osborne et al. |
| 2004/0133266 | A1 | 7/2004 | Cierc et al. |
| 2004/0138737 | A1 | 7/2004 | Davidson et al. |
| 2004/0167607 | A1 | 8/2004 | Frantzen |
| 2005/0171598 | A1 | 8/2005 | Schaeffer |
| 2005/0228484 | A1 * | 10/2005 | Stephens et al. ............ 623/1.16 |
| 2005/0273155 | A1 | 12/2005 | Bahler et al. ............ 623/1.13 |
| 2006/0142836 | A1 | 6/2006 | Hartley et al. ............ 623/1.11 |
| 2007/0050013 | A1 * | 3/2007 | Gross ............ 623/1.24 |
| 2007/0168013 | A1 * | 7/2007 | Douglas ............ 623/1.12 |
| 2008/0009889 | A1 * | 1/2008 | Pokorney et al. ............ 606/155 |
| 2008/0082161 | A1 * | 4/2008 | Woo ............ 623/1.26 |
| 2008/0109058 | A1 * | 5/2008 | Greenberg et al. ............ 623/1.11 |
| 2008/0132993 | A1 * | 6/2008 | Rasmussen et al. ............ 623/1.13 |
| 2009/0062901 | A1 * | 3/2009 | McGuckin, Jr. ............ 623/1.15 |
| 2009/0082846 | A1 * | 3/2009 | Chobotov ............ 623/1.13 |
| 2009/0171429 | A1 | 7/2009 | Wisselink |
| 2009/0222078 | A1 * | 9/2009 | Greenberg ............ 623/1.13 |
| 2010/0042201 | A1 * | 2/2010 | Sherif ............ 623/1.13 |
| 2010/0057096 | A1 * | 3/2010 | Wolf ............ 606/108 |
| 2010/0161028 | A1 * | 6/2010 | Chuter et al. ............ 623/1.13 |

FOREIGN PATENT DOCUMENTS

| | | |
|---|---|---|
| EP | 0 903 118 A2 | 3/1999 |
| EP | 0 903 119 A2 | 3/1999 |
| EP | 0 646 365 B1 | 1/2004 |
| JP | 404231954 A | 8/1992 |
| JP | 407008512 A | 1/1995 |
| WO | WO 98/53761 A1 | 12/1998 |
| WO | WO 99/32050 | 7/1999 |
| WO | WO 99/51165 | 10/1999 |
| WO | WO 02/067815 A1 | 9/2002 |
| WO | WO 03/034948 A1 | 5/2003 |
| WO | WO 03/053287 A1 | 7/2003 |
| WO | WO 03/065933 A1 | 8/2003 |
| WO | WO 03/082153 | 10/2003 |
| WO | WO 2005/027784 | 3/2005 |
| WO | WO 2006/113501 | 10/2006 |
| WO | WO 2009/082654 A1 | 7/2009 |

* cited by examiner

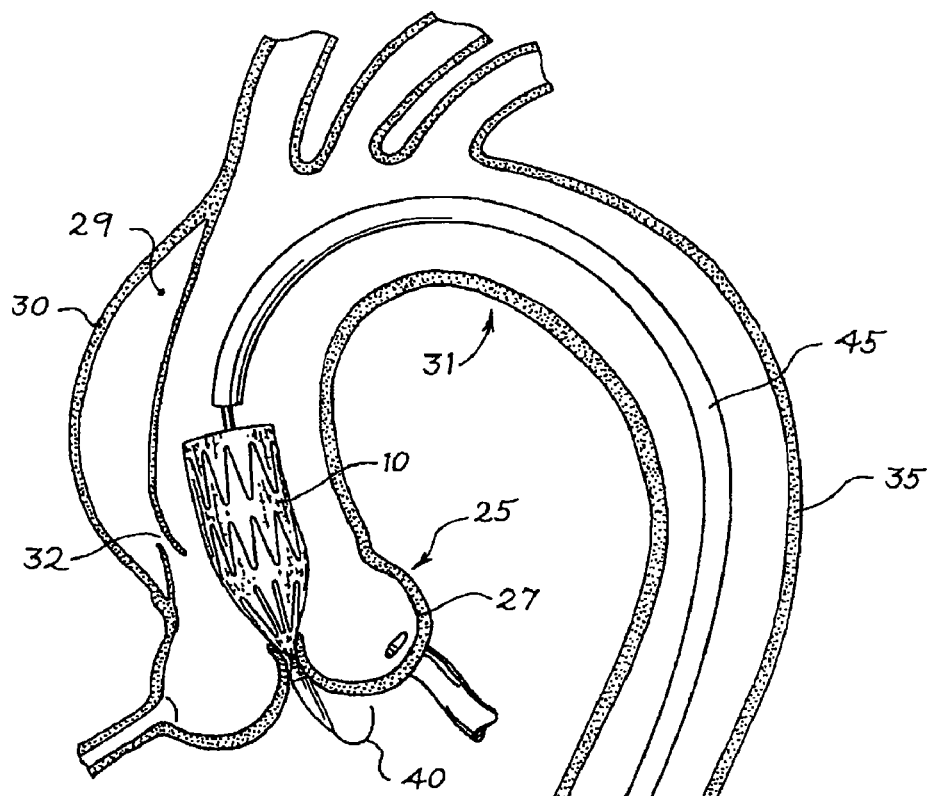
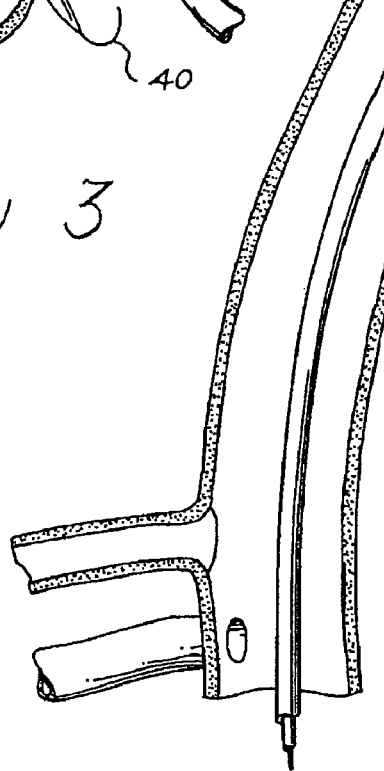

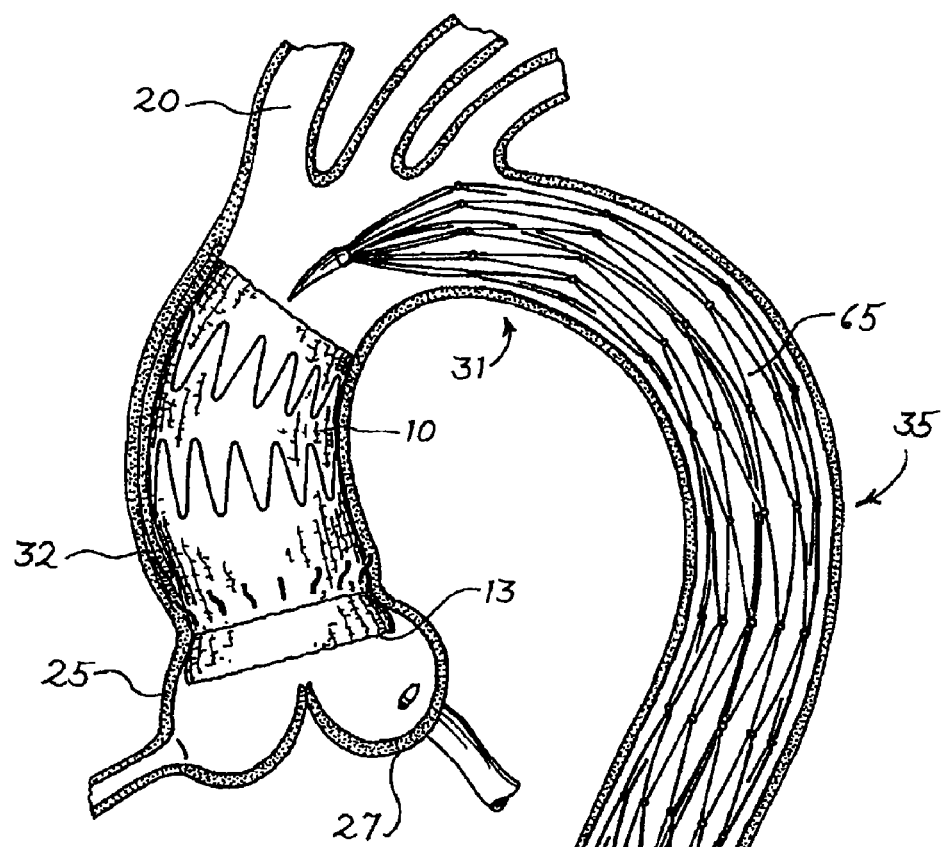
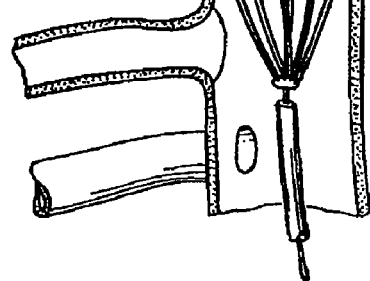

PROSTHESIS FOR IMPLANTATION IN AORTA AND METHOD OF USING SAME

CROSS-REFERENCE TO RELATED APPLICATIONS

This application claims priority to U.S. Provisional Application No. 61/008,949, filed Dec. 21, 2007, which is incorporated herein in its entirety.

BACKGROUND

1. Technical Field

This invention relates to an endovascular prosthesis for implantation within and treatment of a human or animal body for the repair of damaged vessels, ducts, or other physiological passageways. In particular, this invention relates to a device for the treatment of aortic arch disease and more particularly to the treatment of a form of aortic aneurysm known as an aortic dissection in the ascending thoracic aorta.

2. Background Information

The functional vessels of human and animal bodies, such as blood vessels and ducts, occasionally weaken or even rupture. In some case a dissection forms in the aorta. An aortic dissection is a form of aneurysm to the descending aorta in which the wall of the aorta is damaged to such an extent that blood under pressure can get between inner and outer layers of the wall of the aorta to expand part of the wall into an inflated sac of blood which is referred to as a false lumen. The inflated sac of blood or false lumen so formed may extend some distance down the descending aorta and open out into the aorta again further down. The result is an acute aortic dissection, which is also known as an aortic dissection or acute aortic syndrome. Those who suffer from this condition usually have an abnormally weak aortic wall before the dissection occurs. Subjects with thoracic aortic aneurysms are at risk for aortic dissections. In Western European and Australian men who are between 60 and 75 years of age, aortic aneurysms greater than 29 mm in diameter are found in 6.9% of the population, and those greater than 40 mm are present in 1.8% of the population.

Aortic dissections are classified by either the DeBakey System or the Stanford system. A dissection involving both the ascending and descending thoracic aorta is classified as a type I dissection under the DeBakey System. A type II dissection involves a dissection of just the ascending thoracic aorta. Under the Stanford system, type I and II DeBakey dissections are considered type A dissections. A dissection confined to just the descending aorta is considered a type III DeBakey dissection or a Type B Stanford dissection.

If a dissection of the descending thoracic aorta occurs, some patients can be treated with medicaments to handle their blood pressure such that surgery may not be necessary. However, if a dissection of the ascending thoracic aorta occurs, immediate surgery is needed to replace it. One surgical intervention method involves the use of a prosthetic device to provide some or all of the functionality of the original, healthy vessel, and/or preserve any remaining vascular integrity by replacing a length of the existing vessel wall that spans the site of vessel failure.

Ideally, the failed portion of the vessel is sealed off and the weakened vessel walls are supported. For weakened or aneurysmal vessels, even a small leak in the prosthesis may lead to the pressurization of, or flow in, the treated vessel which aggravates the condition the prosthesis was intended to treat. A prosthesis of this type can, for example, treat dissections of the thoracic aorta by implantation at the site of the initial tear of the dissection to seal the tear and thereby stop the flow of blood into the false lumen created by the dissection.

A prosthetic device can be of a unitary construction or be comprised of multiple prosthetic modules. A modular prosthesis allows a surgeon to accommodate a wide variation in vessel morphology while reducing the necessary inventory of differently sized prostheses. For example, aortas vary in length, diameter, and angulation. Prosthetic modules that fit each of these variables can be assembled to form a prosthesis, obviating the need for a custom prosthesis or large inventories of prostheses that accommodate all possible combinations of these variables. A modular system may also accommodate deployment options by allowing the proper placement of one module before the implantation of an adjoining module.

Proper implantation of prosthetic devices used to treat dissections rests on proper placement. Given the relatively small size of the ascending aorta, for instance, ideal anchoring positions for prosthetic devices are few. It is therefore the object of the present invention to provide a prosthetic device with a suitable fixation geometry for secure implantation in the ascending thoracic aorta.

BRIEF SUMMARY

This invention relates to a device for the treatment of aortic arch disease and more particularly to the treatment of a form of aortic aneurysm known as an aortic dissection in the ascending thoracic aorta. A prosthesis for implantation in the ascending aorta is provided that includes a tubular body of a biocompatible graft material, a cuff at the proximal end of the tubular body for biasing pressure onto a sino-tubular junction of the aorta, and at least one stent. The cuff is configured to conform to the sino-tubular junction.

The prosthesis also may include at least one stent that defines a second tubular body for engaging an endoluminal wall. The second tubular body can extend into the descending aorta. The second tubular body can be a bare stent preferably coupled to a tubular body of a biocompatible graft material. The tubular body may have at least one internal socket for receiving one or more secondary prostheses. This structure is useful when secondary stent grafts are deployed in the branch arteries of the aortic arch. The internal sockets may correspond to one or all of the aortic branch arteries.

A method for deploying a prosthesis comprising a tubular biocompatible graft material body with a proximal cuff configured to conform to the sino-tubular junction in the aorta using a deployment device also is provided. The method comprises deploying a guidewire through the aortic valve and implanting the prosthesis in the ascending aorta with the cuff placed in the sino-tubular junction.

BRIEF DESCRIPTION OF THE DRAWINGS

FIG. 3 shows a next stage of deployment of a prosthesis of the present invention where an endovascular prosthesis is partially deployed in the ascending aorta.

FIG. 4B depicts the deployment of a bare stent in the descending aorta.

DETAILED DESCRIPTION OF THE DRAWINGS AND THE PRESENTLY PREFERRED EMBODIMENTS

Figure 1A:
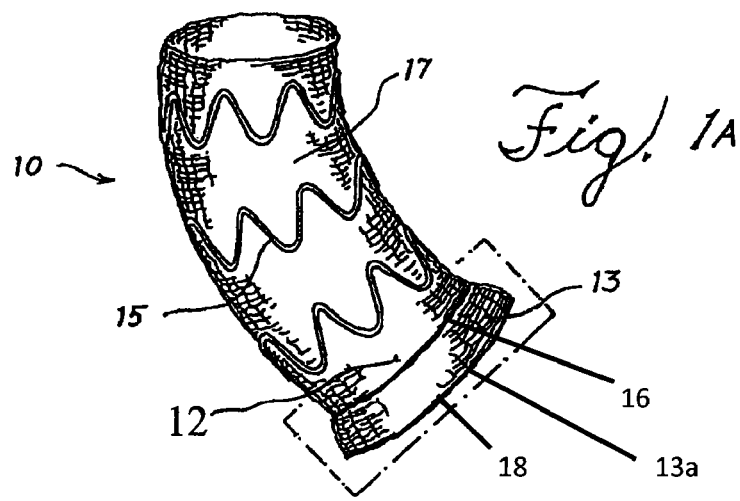
FIG. 1A illustrates an endovascular prosthesis with sino-tubular fixation geometry.

Throughout this specification, when discussing the application of this invention to the aorta or other blood vessels, the term "distal," with respect to a prosthesis, is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

The term "endoluminal" describes objects that are found or can be placed inside a lumen in the human or animal body. The term "endovascular" describes objects that are within a blood vessel. A lumen can be an existing lumen or a lumen created by surgical intervention. This includes lumens such as blood vessels, parts of the gastrointestinal tract, ducts such as bile ducts, parts of the respiratory system, etc. A "prosthetic device" is thus a prosthesis that can be placed inside one of these lumens.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

The term "graft or graft material" means a generally cannular or tubular member which acts as an artificial vessel or prosthesis. A graft by itself or with the addition of other elements, such as structural components, can be an endoluminal prosthesis. Exemplary graft materials are discussed in further detail below.

The term "stent," as used in this disclosure, means any device or structure that adds rigidity, expansion force, or support to a prosthesis. Exemplary stents are discussed in more detail below.

FIGS. 1A through 1E show examples of an endovascular prosthesis 10. FIGS. 1A through 1E each illustrate a prosthesis 10 designed for implantation in the ascending thoracic aorta. As shown, the prosthesis 10 has a tubular body 17 made of at least biocompatible graft material. The prosthesis 10 may include a cuff 13 located at the proximal end 12 of the prosthesis 10. The cuff 13 is designed to bias pressure onto a sino-tubular junction when deployed in the ascending aorta. Preferably, the cuff 13 is configured to conform to the sino-tubular junction which is at the beginning of the ascending aorta in the aortic root. The prosthesis also may include at least one stent 15.

Figure 1B:
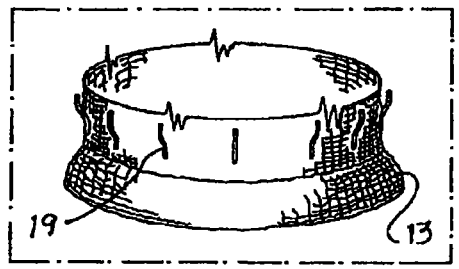
FIG. 1B shows a zoom view of an endovascular prosthesis with barbs attached proximal to the cuff of the prosthesis having a sino-tubular fixation geometry.
Figure 1C:
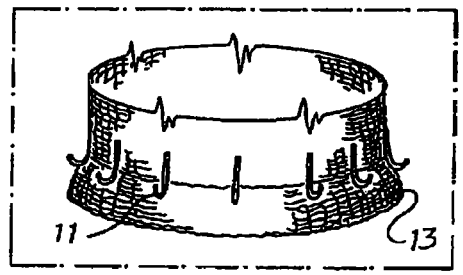
FIG. 1C is a zoom view of an endovascular prosthesis with hooks attached proximal to the cuff.
Figure 1D:
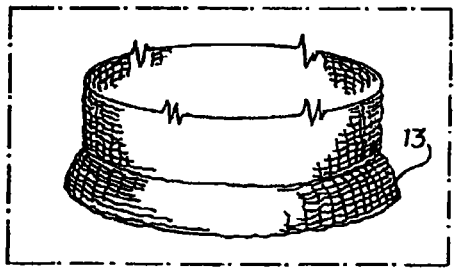
FIG. 1D is a zoom view showing the fixation geometry suitable for placement in the sino-tubular junction of the aortic valve.

FIG. 1D is a zoom view of a cuff 13. As shown, the cuff 13 flares outward from the tubular body in a proximal direction. The cross sectional area of the cuff 13 at its most proximal point may be greater than that of the tubular body.

The cuff may be given a flared shape by two rings-a proximal ring 18 and a distal ring 16. The distal ring 16 may be woven into the graft material where the cuff 13 meets the tubular body 17. The distal proximal ring 18 may be embedded at the proximal end 13a of the cuff 13 and may have a larger diameter than the distal ring 16. Stainless steel, nitinol, or any other material suitable for providing rigidity or semi-rigidity may be used for the rings.

Figure 1E:
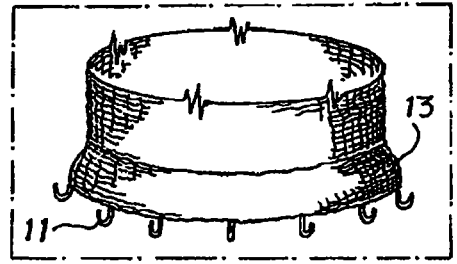
FIG. 1E is a zoom view showing hooks attached to the distal end of the cuff.

As shown in FIG. 1B, cuff 13 includes barbs 19 that are attached distally to the cuff 13 and securable to the ascending aorta. FIGS. 1C and 1E depict additional examples where the cuff 13 includes hooks 11. In FIG. 1C, the hooks 11 are attached distally to the cuff 13. In FIG. 1D, the hooks 11 are attached proximally to the cuff 13. Hooks, barbs, and other structures capable of securing a prosthesis to a vessel may be arranged on the prosthesis in any combination in any location on a cuff 13.

Figure 4A:
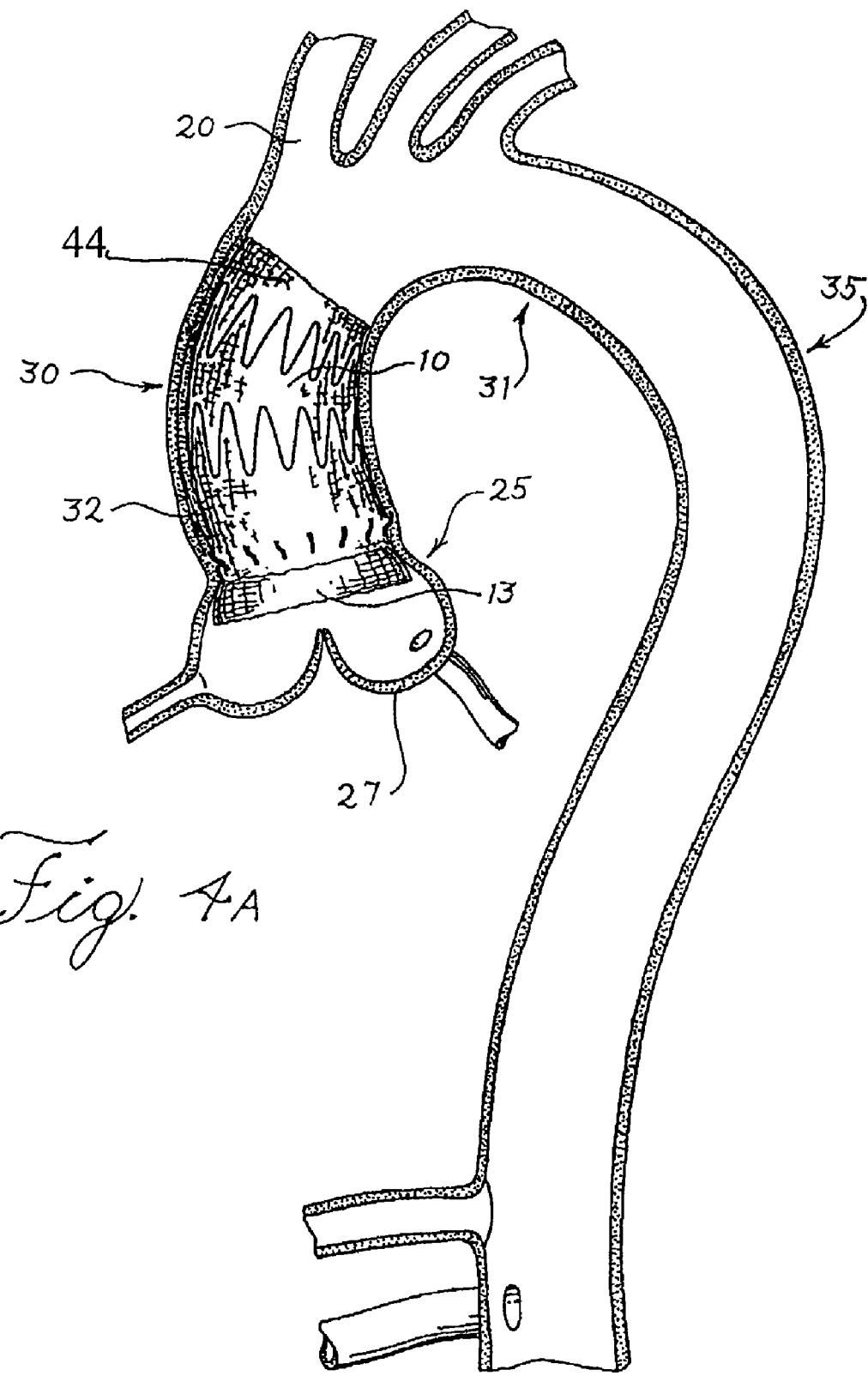
FIG. 4A shows an endovascular prosthesis fully deployed in the ascending aorta with the cuff of a prosthesis placed in the sino-tubular junction.

FIG. 4A shows a prothesis deployed in an ascending aorta 30 to treat a type II DeBakey dissection. The prosthesis 10 extends from the sino-tubular junction 25 to just proximal to the innominate artery 20. The prosthesis 10 may have a length such that its distal end 44 terminates in the descending aorta 35 or in the aortic arch 31.

Figure 4C:
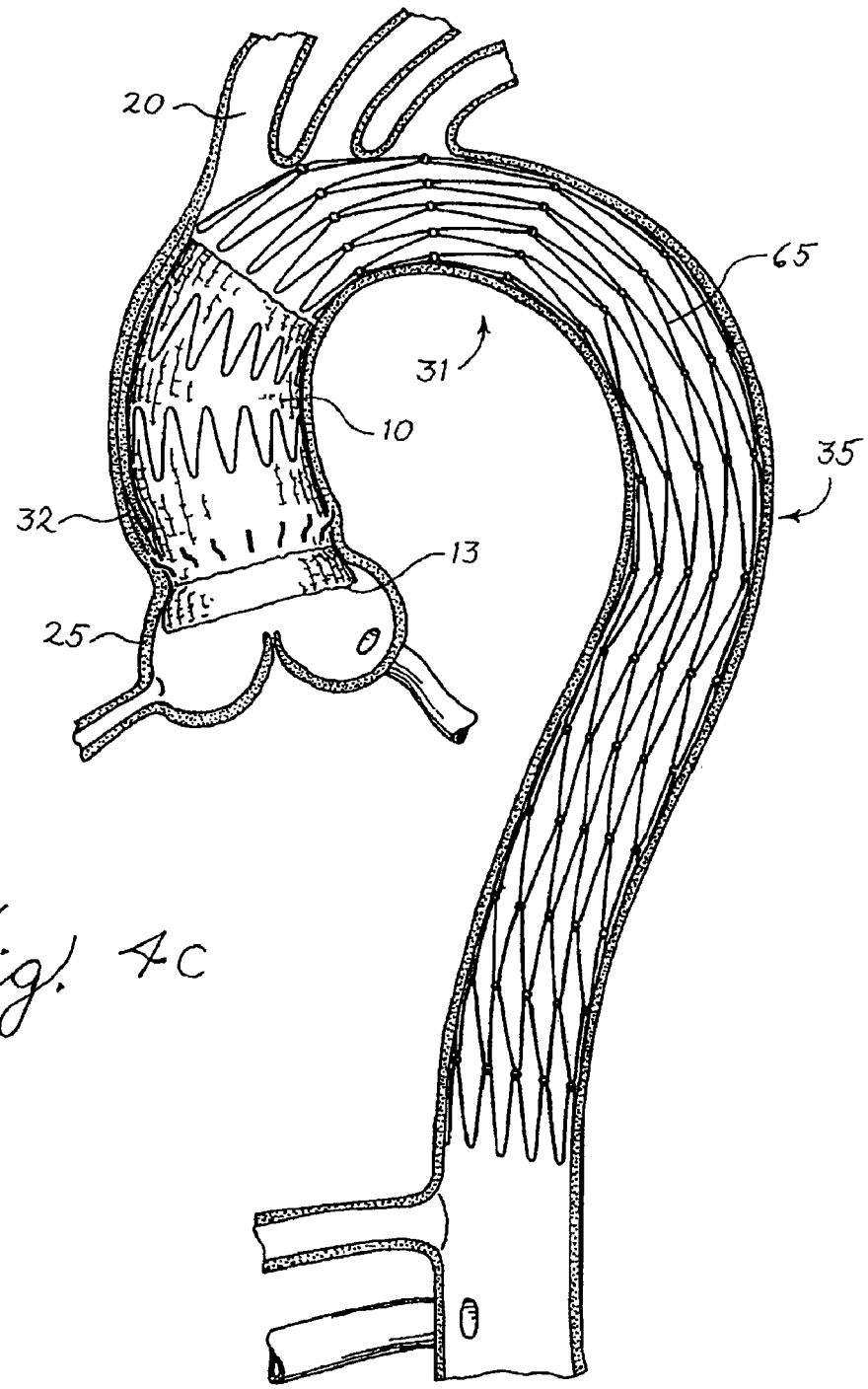
FIG. 4C depicts the bare stent fully deployed and adjacent to the prosthesis.

This invention may also comprise an assembly, such as the stent assembly 65 shown in FIG. 4C. A stent assembly 65 may be a bare stent or a covered stent. Stent assembly and bare stent may be used interchangeably throughout this description. FIG. 4B depicts a bare stent 65 that is being implanted in the aortic arch 31 distal to a prosthesis 10. The bare stent 65 is not yet fully expanded in FIG. 4B. In FIG. 4C, the bare stent 65 is fully expanded such that it biases pressure on the wall of the aortic arch 31 and descending aorta 35.

Figure 5:
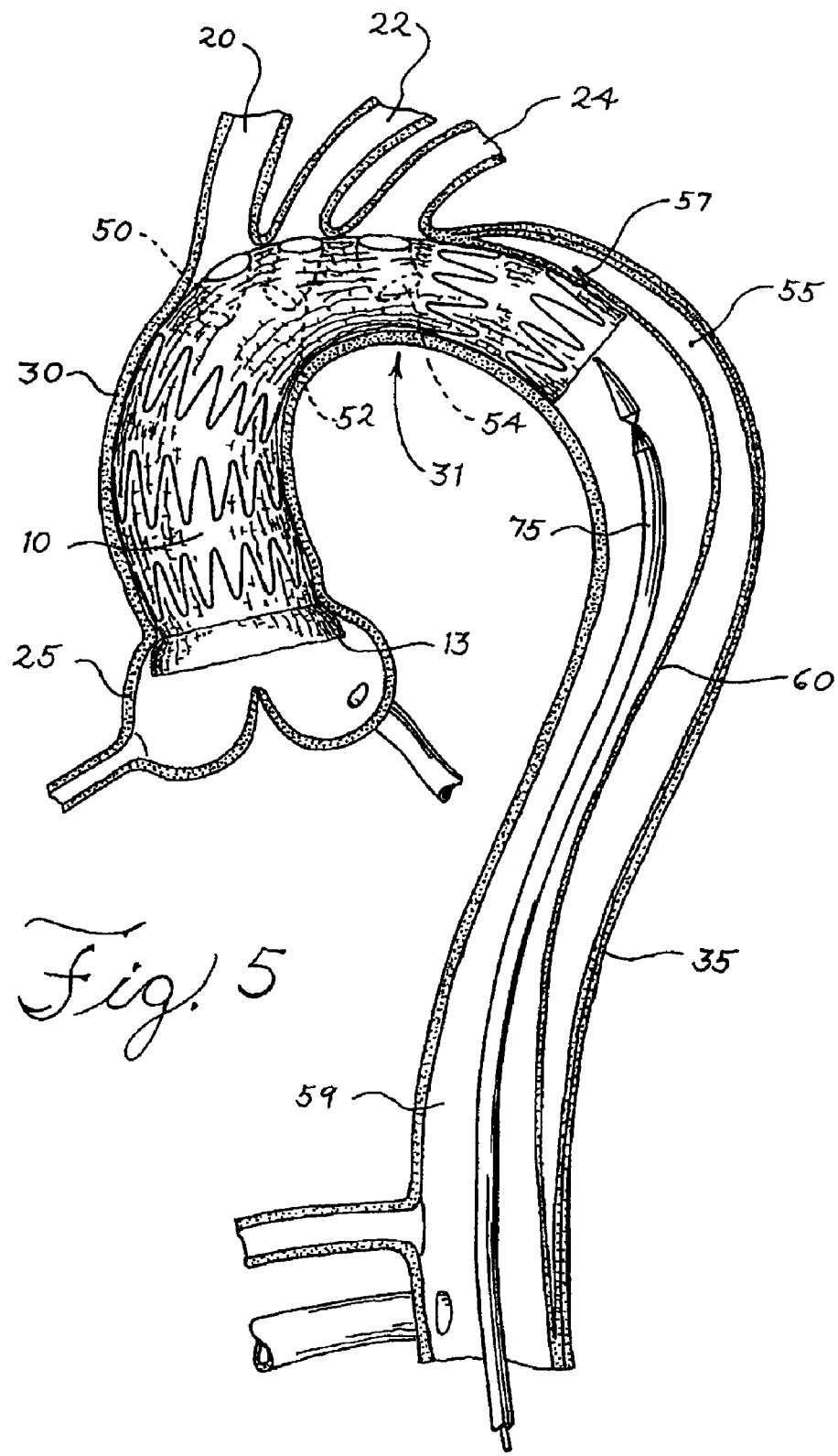
FIG. 5 shows an embodiment of the prosthesis with internal sockets and the prosthesis is being used to treat a type II DeBakey dissection.

FIG. 5 depicts a prosthesis 10 that extends from the sino-tubular junction 25 and through the aortic arch 31 to a point distal to the left subclavian artery 24. The aortic arch 31 is in the upper part of the human chest where it gives off branch arteries 20, 22, and 24 and continues under the neck to the descending aorta 35. As shown in FIGS. 5 through 8, the descending aorta 35 continues down to the diaphragm. The examples shown are useful in treating both types I, II, and III DeBakey dissections.

In another embodiment, there is a prosthesis 10 for implantation in the ascending aorta that comprises a first tubular body 17 comprising biocompatible graft material and at least one stent 15. There is a cuff 13 at the proximal portion 12 of the tubular body 17 for biasing pressure onto a sino-tubular junction of an ascending thoracic aorta and the cuff 13 is configured to conform to the sino-tubular junction. At least one stent defines a second tubular body 65 that is attachable to the first tubular body 17 for engaging an endoluminal wall.

In treating types I, II, and III DeBakey dissections, a prosthesis 10 is implanted in the aortic arch 31. To provide blood flow to the branch arteries, a prosthesis 10, such as the one shown in FIGS. 5-8, includes three sockets 50, 52, and 54 that correspond to a respective branch artery 20, 22, 24. In this instance, socket 50 corresponds to the innominate 20 artery, socket 52 corresponds to the left common carotid 22, and socket 54 corresponds to the left subclavian 24 artery. In some embodiments, prosthesis 10 comprises at least one socket corresponding to a branch artery. Because of their location in the branch artery, the sockets are adapted to receive secondary prostheses. The sockets are preferably made of seamless woven polyester or any other substantially biocompatible graft material, such as the materials described in further detail below.

In some examples, a secondary prosthesis may be implanted in the branch arteries and mated to the prosthesis 10. The secondary prosthesis is deployed preferably within an internal socket in the prosthesis 10. Alternatively, but not presently shown in the figures, a prosthesis may further comprise a helical socket disposed longitudinally along and circumferentially about the tubular body for carrying blood flow to branch arteries.

Figure 6:
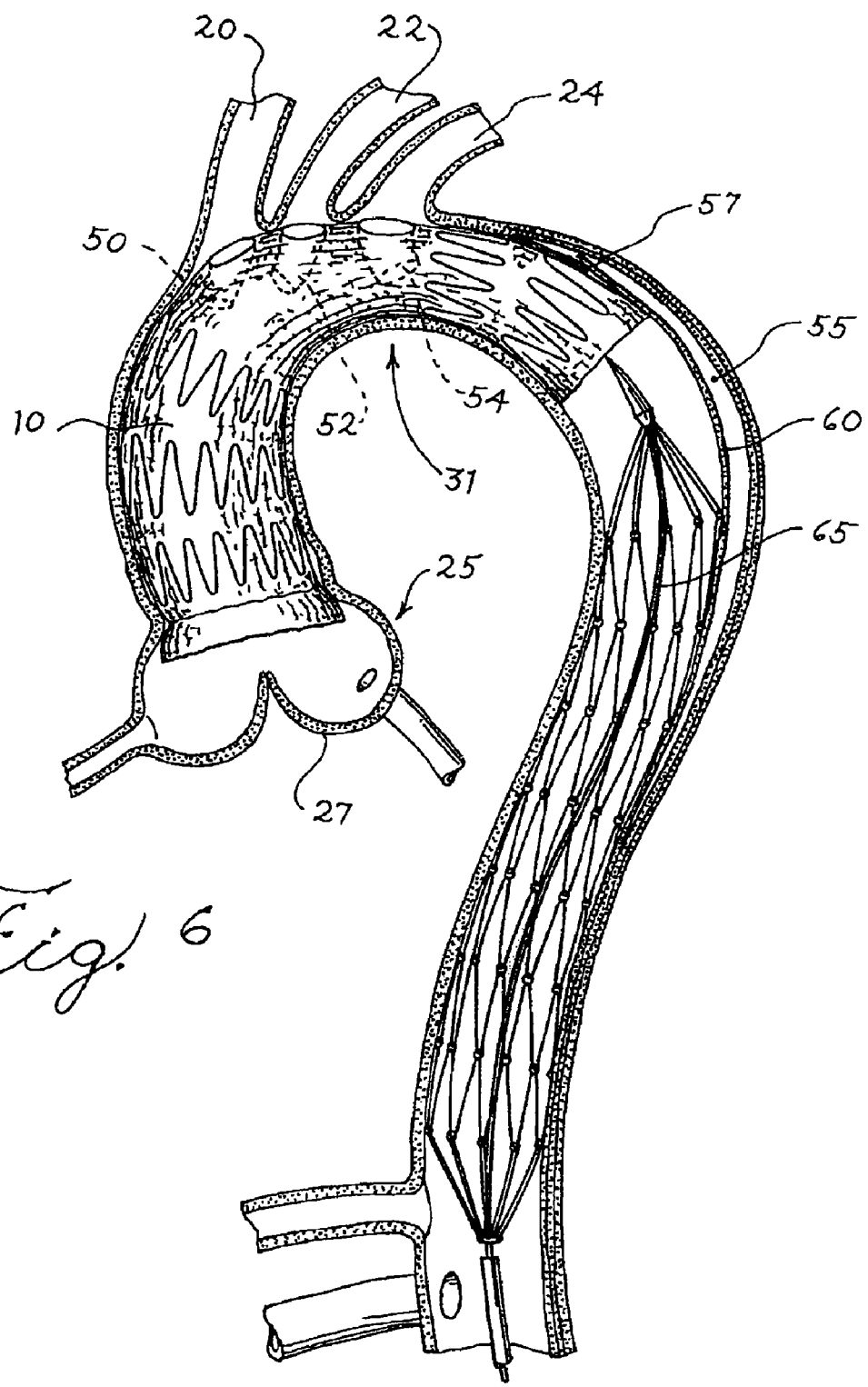
FIG. 6 shows an embodiment with a bare stent being deployed in the descending aorta that will be adjacent to a prosthesis being used to treat a type II DeBakey dissection.
Figure 7:
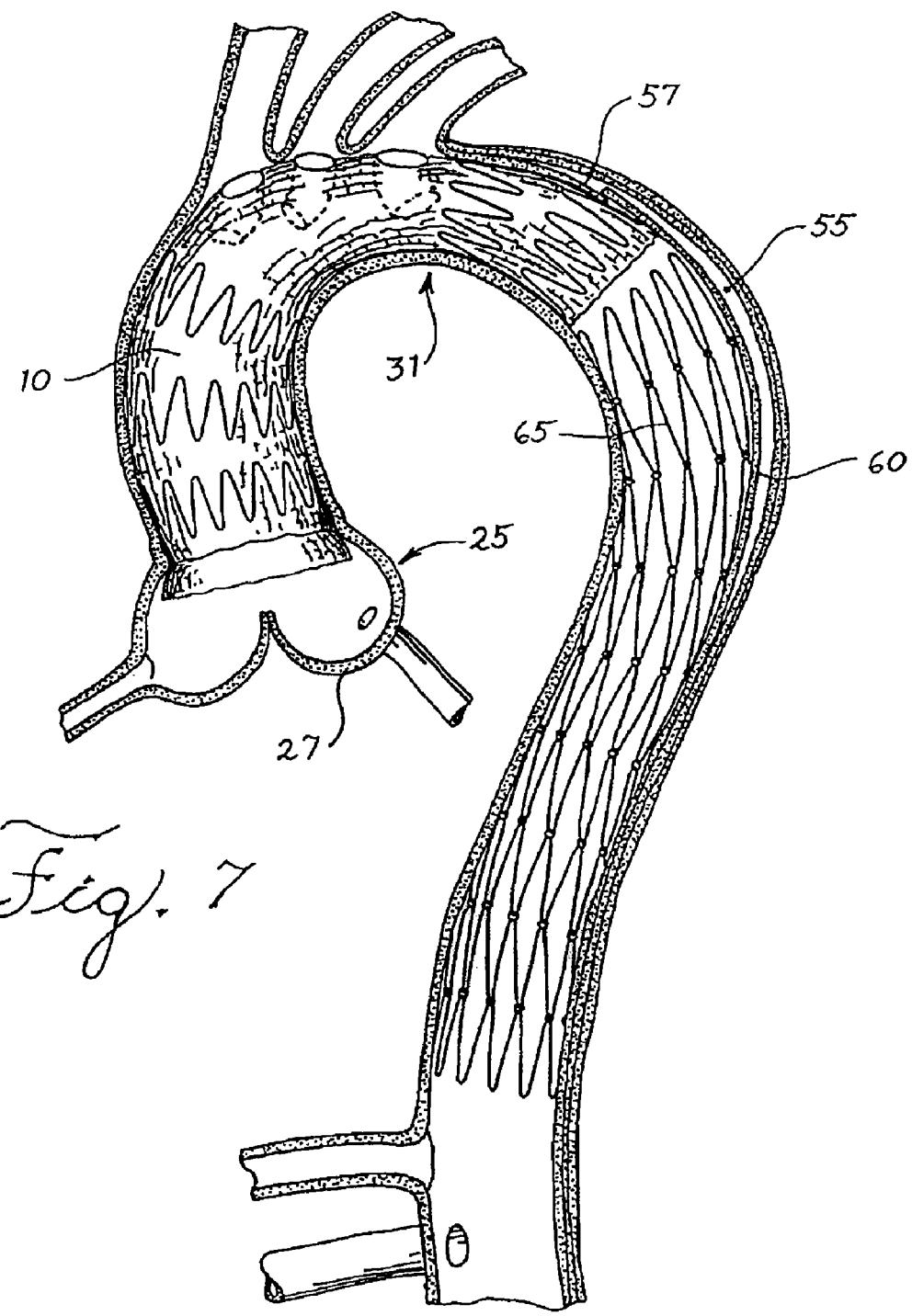
FIG. 7 shows a prosthesis and bare stent fully deployed in a type II DeBakey dissection.
Figure 8:
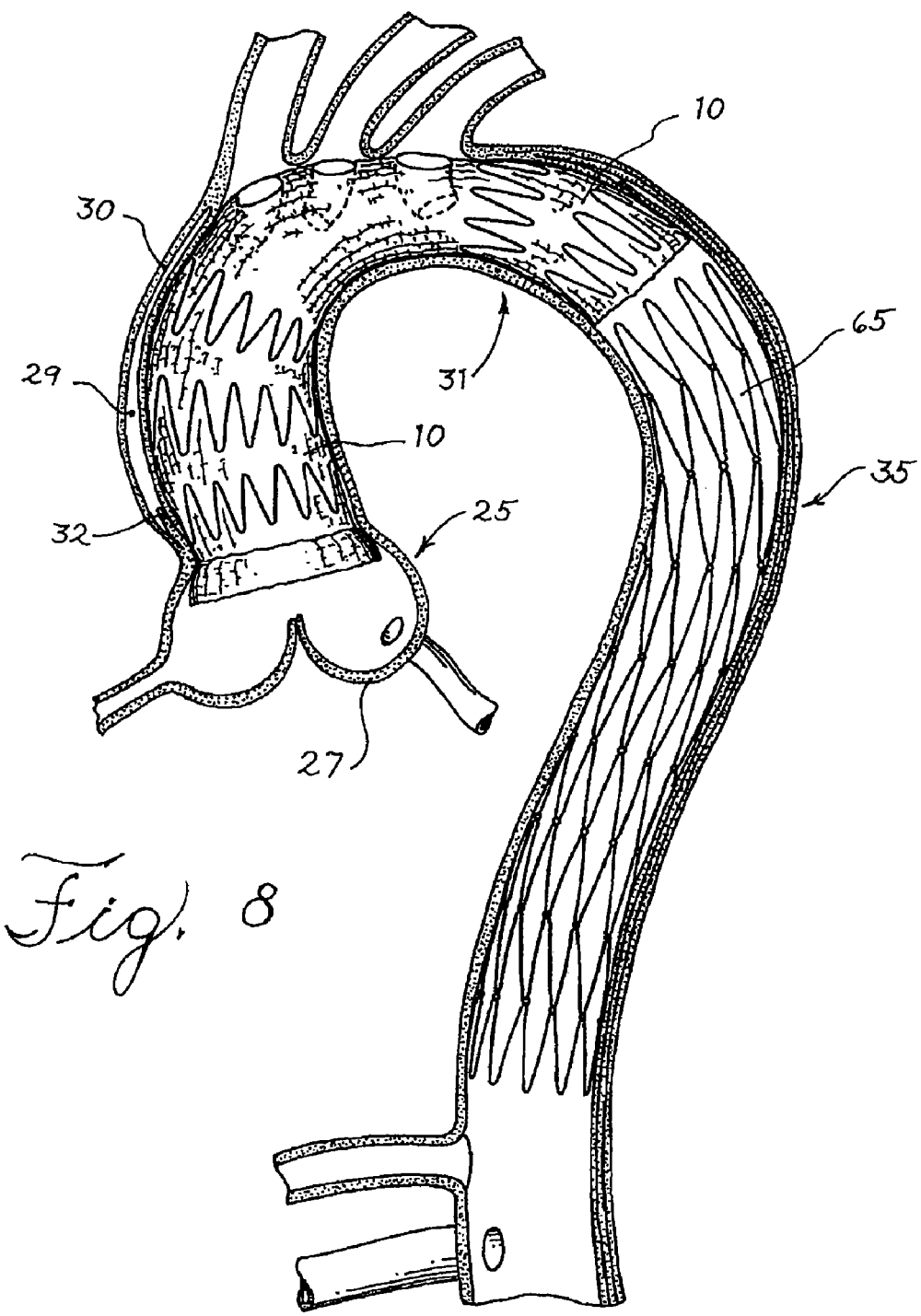
FIG. 8 shows the prosthesis fully deployed in a type III DeBakey dissection.

Another illustration of the present invention is depicted in FIGS. 5-7. A type III DeBakey dissection is represented in FIGS. 5-7. A tear 57 is located in the descending aorta 35 distal to the left subclavian artery 24. FIG. 5 shows the dissection extending along the descending aorta 35 with true 59 and false 55 lumens. The prosthesis 10 with three internal sockets 50, 52, 54 has been deployed already in the ascending aorta 30 and the aortic arch 31. The delivery device 75 is being inserted to the distal end of the prosthesis 10 to begin deployment of the stent assembly 65. Here, a bare stent 65 is used as the stent assembly.

As shown in FIG. 6, the bare stent 65 is placed distal to the prosthesis 10 for treating the dissection in the descending aorta 35. The bare stent 65 comprises a structure that defines a second tubular body for engaging the endoluminal wall 60 of the true lumen 59. As shown here, the stent assembly 65 is a collection of bare stents. The tear 57 through which some blood escapes into the false lumen 55 is blocked by the distal portion of the prosthesis 10 which is comprised of biocompatible graft material. The stent assembly 65 biases sufficient pressure to deflate, to some degree, the false lumen 55 formed by the dissection 55. A fully expanded bare stent 65 is shown in FIG. 7.

Stent assemblies that may be useful in the present invention are comprised preferably of a number of self-expanding stents in a linked arrangement between consecutive stents so that they are coupled together to form the stent assembly 65. In other embodiments, the stent assembly 65 further comprises biocompatible graft material.

The prostheses described here may be deployed in the aorta using a deployment device. The method comprises inserting a guidewire through the aortic valve. A prosthesis comprising a tubular biocompatible graft material body with a proximal cuff configured to conform to the sino-tubular junction is implanted in the ascending aorta. The cuff is placed in the sino-tubular junction and the deployment device is withdrawn. In some embodiments, the prosthesis further comprises at least one socket that corresponds to an aortic branch artery. In such embodiments, the method further comprises deploying a portion of a secondary prosthesis into a socket.

Figure 2:
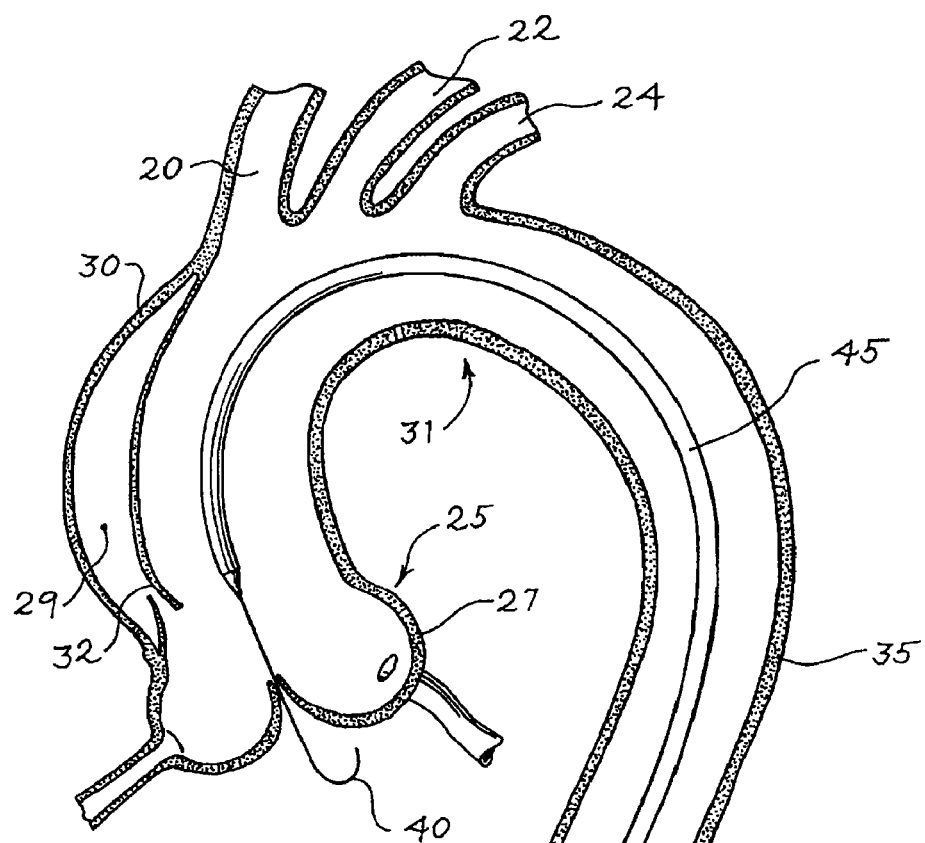
FIG. 2 shows a cross-sectional view of an aorta with a type I DeBakey dissection with a guidewire extending into the aortic valve.

As shown in FIG. 2, a type II DeBakey dissection is present in the ascending aorta 30. A tear 32 is located distal to the sino-tubular junction 25 and a false lumen 29 has formed. A deployment device 45 containing a guidewire 40 and catheter 43 is advanced through the aorta to the sino-tubular junction 25. The proximal tip of the guidewire 40 is advanced through the opening of the aortic valve 27. The procedure is visualized by a surgeon using known imaging techniques.

As shown in FIG. 3, once a deployment device 45 is in a satisfactory position, the sheath of the deployment device 45 is pulled back to expose the prosthesis 10 with the proximal portion at the aortic valve 27. The proximal portion is restrained using a trigger wire mechanism (not shown). Once the trigger wire (not shown) is released, the proximal portion of the prosthesis 10, which contains the cuff 13, expands as shown in FIG. 4a. The cuff 13 engages the walls of the sino-tubular junction 25 and the remainder of the tubular body of the prosthesis 10 engages the walls of the ascending aorta 30. Importantly, the prosthesis 10 closes off the tear 32 and decreases or eliminates the blood flow into the false lumen 29. The volume of the false lumen 29 is decreased further by pressure biased onto the aortic wall by the prosthesis 10. Blood now can flow through the prosthesis 10 to the remainder of the aorta.

A method of the present invention also may be applied in treating dissections that occur in the descending aorta 35. FIG. 5 shows a prosthesis 10 having internal sockets 50, 52, 54 that correspond to the aortic branch arteries 20, 22, 24. This prosthesis 10 has already been implanted in the ascending aorta 30. As this prosthesis comprises biocompatible graft material, the tear 57 in the descending aorta 35 is closed off by the distal part of the prosthesis 10. A second tubular body comprising at least one stent for biasing pressure to a vessel wall is then implanted to treat the dissection in the descending aorta 35. This second tubular body is a stent assembly 65.

A method of the present invention can comprise deploying a guidewire 40 through the aortic valve 27 and implanting in the ascending thoracic aorta a prosthesis. The prosthesis comprises a first tubular biocompatible graft material body 10 and a proximal cuff 13 at the proximal portion 12 of the tubular biocompatible graft material body 10 that is configured to conform to the sino-tubular junction 25. The cuff 13 is placed in the sino-tubular junction 25 and a second tubular body 65 is implanted. The second tubular body 65 is defined by at least one stent and is attachable to the first tubular biocompatible graft material body 10. The second tubular body 65 engages an endoluminal wall once implanted. The deployment device is withdrawn.

FIG. 5 depicts a second deployment device 75 containing a stent assembly 65 being advanced to the distal portion of the tubular body 10. When the second deployment device is in place as shown in FIG. 5, the sheath is pulled back to expose the stent assembly 65. The stent assembly 65 is expanded as shown in FIG. 6 such that it biases pressure on wall 60 to decrease the volume of the false lumen 55. FIG. 7 shows the stent assembly 65 fully expanded and the false lumen 55 substantially deflated. Stent assemblies, such as bare stents, are useful in the present method. The stent assembly 65, preferably, is self expanding in some embodiments. The stent assembly 65 also may be balloon expandable or a combination of self-expanding and balloon expandable stents. The stent assembly 65 may be coupled to the prosthesis 10.

The graft comprises a single material, a blend of materials, a weave, a laminate, or a composite of two or more materials. The graft can also comprise polymer material that may be layered onto the mandrel of the present invention. Preferably, polymers of the present invention, although added in layers onto the mandrel, after curing, result in one layer that encapsulates a stent or woven graft. This also aids in decreasing the incidence of delamination of the resulting endovascular prosthesis.

The graft material may be a woven polyester. For example, the graft material may be polyethylene terephthalate (PET), such as DACRON® (DUPONT, Wilmington, Del.) or TWILLWEAVE MICREL® (VASCUTEK, Renfrewshire, Scotland). Woven polyesters, such as Dacron, possess varying degrees of porosity, where the degree of porosity can be selectively controlled based on the weaving or knitting process that is used to produce the woven polyester. Consequently, depending on the application, the porosity can be adjusted to encourage incorporation of a patient's tissue into the woven graft material, which in turn may more securely anchor the prosthesis within the patient's vessel or lumen. Furthermore, the degree of porosity can also be adjusted to provide a woven graft material that is impermeable to liquids, including blood or other physiological fluids.

The woven graft material may be made of a single material, or it may be a blend, weave, laminate, or composite of two or more materials. The graft material may also include other additives, such as plasticizers, compatibilizers, surface modifiers, biological materials such as peptides and enzymes, and therapeutic agents such as drugs or other pharmaceutically effective medicaments. The therapeutic agents can comprise agents, or combinations thereof, that can affect the cells in a vessel wall, including drugs, chromophores, and nucleic acids. Therapeutic agents also comprise diagnostics such as radiopaque compounds that allow the vessel to be visualized by fluoroscopy or like methods. Therapeutic agents can also comprise antimicrobial agents, such as antibacterial and antiviral agents.

The graft may include a biocompatible polyurethane. Examples of biocompatible polyurethanes include Thoralon® (THORATEC, Pleasanton, Calif.), BIOSPAN®, BIONATE®, ELASTHANE®, PURSIL®, and CARBOSIL® (POLYMER TECHNOLOGY GROUP, Berkeley, CA).

As described in U.S. Pat. No. 6,939,377, incorporated herein by reference, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A polymer graft material can be formed from these two components by dissolving the base polymer and additive in a solvent such as dimethylacetamide (DMAC) and solidifying the mixture by solvent casting or by coagulation in a liquid that is a non-solvent for the base polymer and additive.

The stents used here may be of any configuration. For example a Z-stent may be used. A Z-stent is a stent that has alternating struts and peaks (i.e., bends) and defines a generally cylindrical lumen. A Z-stent 15 is depicted in FIGS. 1A through 1E. The "amplitude" of a Z-stent is the distance between two bends connected by a single strut. The "period" of a Z-stent is the total number of bends in the Z-stent divided by two, or the total number of struts divided by two. Stents may have a wide variety of configurations and may be balloon-expandable or self-expanding. Typically, stents have a circular cross-section when fully expanded, so as to conform to the generally circular cross-section of a body lumen.

The stent may be formed from nitinol, stainless steel, tantalum, titanium, gold, platinum, inconel, iridium, silver, tungsten, cobalt, chromium, or another biocompatible metal, or alloys of any of these. Examples of other materials that may be used to form stents include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

The invention claimed is:

1. A prosthesis for implantation in the ascending aorta comprising:
   a tubular body comprising biocompatible graft material;
   a cuff at the proximal portion of the tubular body for biasing pressure onto a sino-tubular junction of an ascending thoracic aorta and is configured to conform to the sino-tubular junction; and at least one stent;
   wherein the cuff further comprises a distal ring adjacent to the tubular body and a proximal ring; and
   wherein the proximal ring has a larger diameter than the distal ring.

2. The prosthesis of claim 1 wherein the second tubular body is adapted for implantation in the descending aorta.

3. The prosthesis of claim 1 wherein the proximal ring and the distal ring are comprised of nitinol or stainless steel.

* * * * *